US009295716B2

(12) United States Patent
Pettersson et al.

(10) Patent No.: US 9,295,716 B2
(45) Date of Patent: Mar. 29, 2016

(54) METHODS FOR TREATING RESTENOSIS USING ANNEXIN A5

(75) Inventors: Knut Pettersson, Gothenburg (SE); Johan Frostegard, Stockholm (SE); Ola Camber, Bromma (SE)

(73) Assignee: Annexin Pharmaceuticals AB, Veberöd (SE)

(*) Notice: Subject to any disclaimer, the term of this patent is extended or adjusted under 35 U.S.C. 154(b) by 128 days.

(21) Appl. No.: 12/918,709

(22) PCT Filed: Feb. 20, 2009

(86) PCT No.: PCT/GB2009/000454
§ 371 (c)(1),
(2), (4) Date: Aug. 20, 2010

(87) PCT Pub. No.: WO2009/103977
PCT Pub. Date: Aug. 27, 2009

(65) Prior Publication Data
US 2010/0331970 A1    Dec. 30, 2010

Related U.S. Application Data

(60) Provisional application No. 61/030,803, filed on Feb. 22, 2008.

(51) Int. Cl.
| *A61K 38/17* | (2006.01) |
| *A61K 38/49* | (2006.01) |
| *A61L 31/16* | (2006.01) |
| *C07K 14/47* | (2006.01) |
| *A61K 38/00* | (2006.01) |

(52) U.S. Cl.
CPC .............. *A61K 38/49* (2013.01); *A61L 31/16* (2013.01); *C07K 14/4721* (2013.01); *A61K 38/00* (2013.01); *A61L 2300/252* (2013.01)

(58) Field of Classification Search
None
See application file for complete search history.

(56) References Cited

U.S. PATENT DOCUMENTS

| 5,122,154 | A | * | 6/1992 | Rhodes ........................ 623/1.13 |
| 5,545,208 | A | * | 8/1996 | Wolff et al. ................... 623/1.22 |
| 5,922,020 | A |   | 7/1999 | Klein et al. ................... 623/1.15 |
| 6,602,282 | B1 |  | 8/2003 | Yan ............................... 623/1.15 |
| 7,645,739 | B2 |  | 1/2010 | Allison ........................... 514/12 |
| 2005/0037052 | A1 |   | 2/2005 | Udipi et al. ................... 424/426 |
| 2005/0164926 | A1 | * | 7/2005 | Wun ................................ 514/12 |
| 2005/0222030 | A1 |   | 10/2005 | Allison ........................... 514/12 |
| 2006/0083772 | A1 |   | 4/2006 | De Witt et al. ................ 424/426 |
| 2007/0015705 | A1 |   | 1/2007 | Allison |
| 2008/0069823 | A1 | * | 3/2008 | Allison ...................... 424/178.1 |
| 2010/0291064 | A1 | * | 11/2010 | Frostegard et al. ......... 424/94.63 |

FOREIGN PATENT DOCUMENTS

| WO | WO 99/17680 | 4/1999 |
| WO | WO 02/067857 | 9/2002 |
| WO | WO 2005/099744 | 10/2005 |
| WO | WO 2008/008561 | 1/2008 |

OTHER PUBLICATIONS

GenPept Accession No. NP_001145, Nov. 2006, 1 page.*
Dumont et al., Circulation 102:1564-1568, 2000.*
Urban et al., J. Am. Coll. Cardiol. 13:1085-1091.*
Serebruany et al., "Dipyridamole Decreases Protease-Activated Receptor and Annexin-V Binding on Platelets of Poststroke Patients with Aspirin Nonresponsiveness", Cerebrovasc. Dis. 21:98-105, 2006.*
Reutelingsperger et al., "Annexin V, the regulator of phosphatidylserine-catalyzed inflammation and coagulation during apoptosis", CMLS 53:527-532, 1997.*
Gen Bank Accession No. P08758, Feb. 2007, 8 pages.*
Chen et al., Blood 105:3902-3909, 2005.*
Yamanishi et al., Biosci. Biotech. Biochem. 59:1272-1275, 1995.*
Lien et al., Crit. Care 10:317, 2006, 2 pages.*
Gallo et al., "Prolonged Thrombin Inhibition Reduces Restenosis After Balloon Angioplasty in Porcine Coronary Arteries", Circulation 97:581-588, 1998.*
Galán et al., "Antithrombotic action of annexin V proved as efficient as direct inhibition of tissue factor or thrombin", Eur. J. Clin. Invest. 36:633-639, 2006.*
Dictionary definition of "stenosis", obtained from medical-dictionary.thefreedictionary.com/stenosis on Apr. 2, 2015, 6 pages.*
Dictionary definition of "restenosis", obtained from medical-dictionary.thefreedictionary.com/restenosis on Apr. 2, 2015, 2 pages.*
Bhadra et al., "Pegnology: a review of PEG-ylated systems," *Pharmazie*, 57:5-29, 2002.
Blindt et al., "Development of a new biodegradable intravascular polymer stent with simultaneous incorporation of bioactive substances," *Int. J. Artif. Organs*, 22:843-853, 1999.
Bravata et al., "Systematic review: the comparative effectiveness of percutaneous coronary interventions and coronary artery bypass graft surgery," *Ann. Intern. Med.*, 147(10):703-716, 2007.
Cederholm and Frostegård, "Annexin A5 as a novel player in prevention of atherothrombosis in SLE and in the general population," *Ann. NY Acad. Sci*, 1108:96-103, 2007.
Cederholm et al., "Decreased binding of annexin v to endothelial cells: a potential mechanism in atherothrombosis of patients with systemic lupus erythematosus," *Arterioscler. Thromb. Vasc. Biol.*, 25(1):198-203, 2005.
Harris et al., "Pegylation: a novel process for modifying pharmacokinetics," *Clin. Pharmacokinet*, 40:539-551, 2001.
Hirata et al., "Noninvasive diagnosis of restenosis by transthoracic Doppler echocardiography after percutaneous coronary intervention: comparison with exercise TI-SPECT," *J. Amer. Soc. Echocardiography*, 19:165-171, 2006.

(Continued)

*Primary Examiner* — David J Steadman
(74) *Attorney, Agent, or Firm* — Parker Highlander PLLC (57) ABSTRACT

A method for the prophylaxis or treatment of restenosis comprising administering a therapeutically effective amount of Annexin A5 or a functional analog or variant thereof to a patient in need of such treatment. A method for the treatment of stenosis in a patient comprising performing an intervention for the treatment of stenosis in conjunction with administering a therapeutically effective amount of Annexin A5 or a functional analog or variant thereof. A pharmaceutical composition comprising a therapeutically effective amount of Annexin A5 or a functional analog or variant thereof for the prophylaxis or treatment of restenosis. A drug eluting stent, wherein the drug is Annexin A5 or a functional analog or variant thereof, and a method of making such a stent.

19 Claims, 3 Drawing Sheets

(56) References Cited

OTHER PUBLICATIONS

Holte et al., "Direct visualization of a significant stenosis of the right coronary artery by transthoracic echocardiography. A case report," *Cardiovascular Ultrasound*, 5:33, 2007.
Jasti et al., "Correlations between fractional flow reserve and intravascular ultrasound in patients with an ambiguous left main coronary artery stenosis," *Circulation*, 110:2831-2836, 2004.
Kenis et al., "Annexin A5: shifting from a diagnostic towards a therapeutic realm," *CMLS Cellular and Molecular Life Sciences*, 64(22):2859-2862, 2007.
Kozlowski et al., "Development of pegylated interferons for the treatment of chronic hepatitis," *C. Biodrugs*, 15:419-429, 2001.
Kozlowski et al., "Improvements in protein PEGylation: pegylated interferons for treatment of hepatitis C," *J. Control Release*, 72:217-224, 2001.
Motwani and Topol, "Aortocoronary saphenous vein graft disease: pathogenesis, predisposition, and prevention," *Circulation*, 97(9):916-931, 1998.
Ong and Serruys, "Drug-eluting stents: current issues," *Curr. Issues Cardiol.*, 32:372-377, 2005.
Pires et al., "Drug-eluting stents studies in mice: do we need atherosclerosis to study restenosis?," *Vascul. Pharmacol.*, 44(5):257-264, 2006.
Rand, "Antiphospholipid antibody-mediated disruption of the annexin-V antithrombotic shield: a thrombogenic mechanism for the antiphospholipid syndrome," *J. Autoimmun.*, 15(2):107-111, 2000.
Reddy, "Controlled-release, pegylation, liposomal formulations: new mechanisms in the delivery of injectable drugs," *Ann. Pharmacother.*, 34:915-923, 2000.
Roberts et al., "Chemistry for peptide and protein PEGylation," *Adv. Drug Deliv.*, 54:459-476, 2002.
Shen et al., "Diannexin, a novel annexin V homodimer, protects rat liver transplants against cold ischemia-reperfusion injury," *Am. J. Transplant.*, 7(11):2463-2471, 2007.
Smith et al., "ACC/AHA/SCAI 2005 Guideline Update for Percutaneous Coronary Intervention-Summary Article: A Report of the American College of Cardiology/American Heart Association Task Force on Practice Guidelines (ACC/AHA/SCAI Writing Committee to Update the 2001 Guidelines for Percutaneous Coronary Intervention)," *J. Am. Coll. Cardiol.*, 47(1):216-235, 2006.
Teoh et al., "Diannexin, a novel annexin V homodimer, provides prolonged protection against hepatic ischemia-reperfusion injury in mice," *Gastroenterology*, 133(2):632-646, 2007.
Thiagarajan and Benedict, "Inhibition of Arterial Thrombosis by Recombinant Annexin V in a Rabbit Carotid Artery Injury Model," *Circulation*, 97(7):2339-2347, 1997.
Van Ryn-McKenna et al., "The effect of heparin and annexin V on fibrin deposition after injury in the jugular veins of rabbits," *Thrombosis Research*, 65(1):S44, 1992.
Van Tits et al., "Plasma annexin As level relates inversely to the severity of coronary stenosis," *Biochemical and Biophysical Research Communications*, 356(3):674-680, 2007.
Vermes et al., "A novel assay for apoptosis. Flow cytometric detection of phosphatidylserine expression on early apoptotic cells using fluorescein labelled Annexin V," *J. Immunol. Methods*, 184(1):39-51, 1995.
Veronese, "Peptide and protein PEGylation: a review of problems and solutions," *Biomaterials*, 22:405-417, 2001.
Vogt et al., "Long-term assessment of a novel biodegradable paclitaxel-eluting coronary polylactide stent," *Eur. Heart. J.*, 25:1330-1340, 2004.
Zhang et al., "Vein graft neointimal hyperplasia is exacerbated by tumor necrosis factor receptor-1 signaling in graft-intrinsic cells," *Arterioscler. Thromb. Vasc. Biol.*, 24(12):2277-2283, 2004.
Zou et al., "Mouse model of venous bypass graft arteriosclerosis," *Am. J. Pathol.*, 153(4):1301-1310, 1998.
Korotaeva et al., "The catalytically active secretory phospholipase A2 type IIA is involved in restenosis development after PTCA in human coronary arteries and generation of atherogenic LDL", *Molecular and Cellular Biochemistry*, 270: 107-113, 2005.
Moon et al., "Endovascular drug-coated stenting of basilar artery stenosis: a case report and literaure review", *Korean Circulation J.*, 34(9):913-918, 2004. (English Abstract).
NCBI Accession No. NP_001145.1, "annexin 5 [*Homo sapiens*]", dated Dec. 3, 2007.

\* cited by examiner

SEQUENCE LISTING

```
<160> NUMBER OF SEQ ID NOS: 1

<210> SEQ ID NO 1
<211> LENGTH: 320
<212> TYPE: PRT
<213> ORGANISM: Homo sapiens
<220> FEATURE:
<221> NAME/KEY: misc_feature
<223> OTHER INFORMATION: Human Annexin A5

<400> SEQUENCE: 1

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
```

```
                                -continued
145                 150                 155                 160
Arg Asp Pro Asp Ala Gly Ile Asp Glu Ala Gln Val Glu Gln Asp Ala
            165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
            195                 200                 205

Val Phe Asp Lys Tyr Met Thr Ile Ser Gly Phe Gln Ile Glu Glu Thr
            210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
            245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
            275                 280                 285

Arg Lys Asn Phe Ala Thr Ser Leu Tyr Ser Met Ile Lys Gly Asp Thr
            290                 295                 300

Ser Gly Asp Tyr Lys Lys Ala Leu Leu Leu Leu Cys Gly Glu Asp Asp
305                 310                 315                 320
```

METHODS FOR TREATING RESTENOSIS USING ANNEXIN A5

This application is a national phase application under 35 U.S.C. §371 of International Patent Application No. PCT/GB2009/000454 filed Feb. 20, 2009 claims priority to U.S. Provisional Patent Application No. 61/030,803 filed Feb. 22, 2008. The entire text of the above-referenced disclosures are specifically incorporated herein by reference without disclaimer.

FIELD OF THE INVENTION

The invention relates to novel methods and compositions for the prophylaxis or treatment of restenosis, such as restenosis following bypass grafting and or percutaneous coronary or peripheral catheter-based interventions aiming at restoring blood flow to ischaemic tissue.

BACKGROUND TO THE INVENTION

The listing or discussion of an apparently prior-published document in this specification should not necessarily be taken as an acknowledgement that the document is part of the state of the art of is common general knowledge.

Ischaemic heart disease (IHD) is normally the result of atherosclerosis in the coronary arteries. Atherosclerosis is a disease of the arterial intima, and starts as focal deposition of lipid material and inflammatory cells. When these lipid laden lesions become advanced, they may become stenosing (i.e. cause narrowing of the blood vessel) and can thus limit blood flow to parts of the myocardium. Atherosclerosis occurs also in other arteries and can lead to stenosis in the vessels to especially the legs, brain and kidneys. This blood flow limitation can cause ischaemic pain, such as angina pectoris and intermittent claudication.

Another consequence of atherosclerosis is that the lesions can become unstable and rupture, leading to the formation of an arterial thrombus at the site of rupture. This thrombus severely compromises oxygen supply to the downstream tissue and will, unless the thrombus is resolved, lead to infarction of the ischaemic tissue (myocardial infarction, stroke, etc.). Myocardial infarction and stroke are the two most common causes of death worldwide.

Restoring normal blood supply to ischaemic tissue is the most important acute goal for the treatment of ischaemic disorders, this can be achieved by medication or by intervention. In patients with acute arterial thrombotic events such as acute myocardial infarction, it is important to restore blood flow to the ischaemic tissue as quickly as possible, in order to reduce the consequences of the thrombotic event, and surgical intervention is common in this situation. Patients with stable angina pectoris or other ischaemic disorders that cannot be adequately controlled with drugs can also be treated surgically.

Surgical interventions, such as for coronary revascularisation, are performed by either bypass grafting (such as coronary artery bypass grafting, CABG) or by catheter based interventions. In the case of bypass surgery such as CABG, a mammary artery is exposed, its distal end removed from the breast and sutured into a position distal to the stenosed segment of the coronary artery, thus allowing perfusion of the ischaemic tissue. If the mammary artery cannot be used, or if multiple bypasses are required, the surgeon will use veins from the legs (vein grafts). In this case, a vein segment is removed and placed from the aorta to a position distal to the stenosis.

During catheter based interventions, such as PCI (percutaneous coronary intervention), a balloon catheter is typically inserted through a femoral artery and guided into the stenotic segment, where the balloon is inflated and the stenotic segment thus dilated. This is also known as balloon angioplasty. Other procedures that are done during PCI may include implantation of a stent, or atherectomy, such as rotational or laser atherectomy (removal of atheromatous plaque material). To improve efficacy of the intervention, a stent catheter can be used to implant a stent. In this case, the catheter will also place a metal stent to support the artery wall to maintain lumen calibres.

Interventions intended to restore normal blood flow to ischemic tissue can result in restenosis, caused by the formation of a neointima or neointimal thickening. The underlying cause is vascular smooth muscle injury and disruption of the integrity of the endothelial lining. The process is also characterised by the presence and activity of inflammatory cells and eventual co-morbidities the patient suffers. The underlying molecular mechanisms of the processes of development of the primary stenosis and the secondary restenosis are different, but there is considerable overlap between the two.

Bypass grafting is an effective intervention, but a common complication is the so called restenosis, the rapid development of a neointima that will lead to the formation of a new stenosis in the graft vessel, often resulting in the need to perform a repeat revascularisation procedure. This is especially common in vein grafts, where approximately 15% of grafts occlude during the first year, and by 10 years 50% of the graft vessels are stenotic (Motwani and Topol, 1998). Vein graft failure can be considered as an injury-induced inflammatory disease, including macrophage infiltration and activation and medial smooth muscle cell activation (Zhang et al., 2004).

Also after PCI is restenosis a common complication. It is more common to perform a repeat revascularisation procedure after PCI than after CABG; the absolute rates at 5 years were 46.1% after balloon angioplasty, 40.1% after PCI with stents, and 9.8% after CABG (Bravata et al., 2007).

Proliferation of smooth muscle cells of a matrix synthesising phenotype is an important factor in the process leading to neointima formation. A recent development that effectively reduces restenosis is the so called drug eluting stents (DES). These stents are coated with polymers that contain cytostatic agents (e.g., rapamycin), that effectively inhibits the proliferative response to the surgical intervention. In patients receiving DES, restenosis occurs typically with an incidence below 4%. However, the DES stents do not become fully integrated into the vessel wall, and they are associated with an increased risk for thrombus formation, that cannot be effectively controlled with drugs. In fact, the advantage of DES as concerns restenosis do not lead to a significant improvement in prognosis for the patient, as increased risk for thrombosis offsets this effect. In fact, there are now recommendations to use DES with caution, and recommendations to increase antithrombotic therapy has also been issued (Smith et al., 2006).

The restenotic lesions are inflammatory lesions that at least superficially have similarities to the primary atherosclerotic lesions. The dominating cells are smooth muscle cells, but also macrophages/foam cells and T-lymphocytes are present in restenosis lesions. CABG and PCI are effective treatments for stenosis, and there has been some advantage in medical approaches to limit intervention associated complications, but effective treatments that prevent restenosis effectively would further improve the treatment. Even in the case of DES, it would be an advantage if the stents could be coated with an effective anti-restenotic agent that does not lead to an increased risk for the formation of arterial thrombi.

From the above summary, it becomes evident that an effective treatment that reduces the formation of restenosis is a therapeutic opportunity for disease conditions where revascularisation procedures are performed, independent of whether the technique used to obtain revascularisation is bypass grafting or by balloon dilatation of the stenosed vessel segment, with or without stent placement.

Annexin A5 is an endogenous protein that binds to charged phospholipids such as phosphatidylserine (PS) (Cederholm and Frostegard, 2007). Annexin A5 is a potent anti-thrombotic agent (Thiagarajan and Benedict, 1997), and it is proposed that Annexin A5 by binding to exposed PS can form a 'protective shield' that can inhibit the effects of PS on thrombosis formation (Rand, 2000).

It has been shown that in addition to anti-platelet and anti-coagulant effects of Annexin A5, this protein and an analogue thereof, the Annexin A5 dimer diannexin, is effective in preventing reperfusion injury in the liver (Teoh et al., 2007), and it improved the outcome of rat liver transplants (Shen et al., 2007). Interestingly, in both these studies the treatments were associated with a reduced inflammatory activity in the hepatic endothelium, measured as reduced expression of adhesion molecules, that is Annexin A5 has anti-inflammatory effects. It was suggested that diannexin improved the survival of the liver transplants by an anti-thrombotic effect leading to maintained blood supply to the liver (Shen et al., 2007). It has earlier been suggested that Annexin A5 can be used to stabilise atherosclerotic lesions in coronary arteries in patients, which should reduce the risk for myocardial infarction in these patients (Cederholm et al., 2005; WO 2005/099744).

SUMMARY OF THE INVENTION

A first aspect of the invention provides a method for the prophylaxis or treatment of restenosis comprising administering a therapeutically effective amount of Annexin A5 or a functional analogue or variant thereof to a patient in need of such treatment.

A second aspect of the invention provides a method for the treatment of stenosis in a patient comprising performing an intervention for the treatment of stenosis in conjunction with administering a therapeutically effective amount of Annexin A5 or a functional analogue or variant thereof.

A third aspect of the invention provides pharmaceutical composition comprising a therapeutically effective amount of Annexin A5 or a functional analogue or variant thereof for the prophylaxis or treatment of restenosis.

A fourth aspect of the invention provides a drug eluting stent, wherein the drug is Annexin A5 or a functional analogue or variant thereof.

A fifth aspect of the invention provides a method for making a stent for delivering Annexin A5 or a functional analogue or variant thereof to a patient, the method comprising incorporating Annexin A5 or a functional analogue or variant thereof into or onto a stent body.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

DETAILED DESCRIPTION OF THE INVENTION

Here, the inventors show that Annexin A5 can reduce the formation of a neointima in two mouse models of restenosis. Thus, Annexin A5 or analogues thereof present a new treatment modality with anti-restenotic properties that can reduce the number of restenosis-related complications in patients undergoing bypass grafting or angioplasty procedures for revascularisation of ischemic tissue. There are no previous reports to show that Annexin A5 has anti-restenotic properties. Annexin A5 can therefore be used to prevent restenosis. Annexin A5 can be administered systemically, and it can also be used as an anti-restenotic agent in drug eluting stents.

In a first aspect, the invention provides a method for the prophylaxis or treatment of restenosis comprising administering a therapeutically effective amount of Annexin A5 or a functional analogue or variant thereof to a patient in need of such treatment.

Put another way, the first aspect of the invention provides Annexin A5 or a functional analogue or variant thereof for use in the prophylaxis or treatment of restenosis. By "prophylaxis" we include prevention, particularly prevention of the development of restenosis, or reduction in the development of restenosis (primary prophylaxis) and secondary prophylaxis, in which restenosis has already occurred, but the patient is protected against worsening of the condition, or the condition worsens more gradually or to a reduced extent. By "treatment" we include the meaning that existing restenosis can be reversed, either partially or totally, in the patient.

The patient is typically a human patient. Alternatively, the patient may be a non-human animal, such as a domestic animal (for example, cat, dog, rabbit, cow, sheep, pig, mouse or other rodent).

Restenosis may occur following an intervention aimed at restoring normal blood flow to ischemic tissue, such as a revascularisation procedure that has been used to treat stenosis of a blood vessel, or the build-up of atheromatous plaque in a blood vessel. Stenosis or vessel obstruction due to atheroma can be diagnosed by a physician according to means known in the art. Coronary stenosis is typically assessed by coronary angiography or intravascular ultrasound (IVUS). The latter is also used to quantify arterial plaque. Jasti et al (2004) *Circulation* 110: 2831-2836 describe parameters that can be measured by IVUS, and also quantitative coronary angiography. Suitable parameters of a target lesion and reference segment that can be measured by IVUS are: (1) minimum and maximum lumen diameters (mm); (2) minimal lumen cross-sectional area (MLA, $mm^2$); (3) plaque plus media cross-sectional area (CSA, $mm^2$) equal to the external elastic membrane cross-sectional area (EEM CSA) minus the MLA; (4) cross-sectional narrowing (CSN), which was calculated as plaque plus media CSA divided by the EEM CSA; (5) the reference segment, which was the normal-looking artery cross section located proximal or distal to the stenosis; typically average of measurements proximal and distal to the stenosis can be determined; and (6) area stenosis (AS), calculated as the reference-lumen CSA-lesion MLAx100/reference-lumen CSA. Mean lumen diameter (MLD) of $\leq 2.8$ mm or mean lumen area of $\leq 5.9$ $mm^2$ were indicative of a clinically significant stenosis which warrants intervention in this study. The skilled person will appreciate that different cut-off values may be appropriate for diagnosis of stenosis in different vessels. A reduction of the lumen to 50% of the reference segment is often considered as a clinically relevant stenosis.

Non-invasive means of diagnosing stenosis are also known. Holte et al (2007) *Cardiovascular ultrasound* 5: 33 describe transthoracic Doppler echocardiography for direct visualisation of coronary segments and assessment of the coronary velocity flow reserve (CVFR). By this technique, coronary stenoses typically show local flow acceleration and turbulence expressed as colour aliasing by colour flow Doppler and accelerated flow velocities across the stenosis. To assess the severity of the stenoses, flow acceleration can be quantified by comparing flow velocities at the site of aliasing with nearest upstream nonaccelerated prestenotic flow velocities. A maximal-to-prestenotic peak diastolic flow velocity ratio greater than 2.0 predicts significant stenosis with high sensitivity and specificity.

Stenosis is not limited to coronary arteries and may occur in cerebral blood vessels as well as other peripheral arteries such as renal arteries and arteries of the limbs. Stenosis may be diagnosed in such vessels in a similar manner to diagnosis in coronary vessels, or by functional testing such as treadmill exercise.

Typically, restenosis may become apparent within weeks, months or years of the intervention aimed at restoring normal blood flow to ischemic tissue and, if untreated, progress over a time frame of weeks, months or years. Restenosis may or may not be diagnosed during follow-up after the intervention, and may first be noticed when it results in clinical complications such as angina, thrombosis or infarction. Restenosis is typically diagnosed by a physician according to the same means used to diagnose stenosis. Typically, coronary restenosis may be assessed by coronary angiography, IVUS or by non-invasive means such as transthoracic Doppler echocardiography. Similar clinical parameters as described above in relation to diagnosis of stenosis are also used for the diagnosis of restenosis. A maximal-to-prestenotic peak diastolic flow velocity ratio greater than 2.0 determined by transthoracic Doppler echocardiography may be indicative of restenosis, as described in Nolte et al., supra. Hirata et al (2006) *J. Amer. Soc. Echocardiography* 19:165-191 describe non-invasive diagnosis of restenosis by transthoracic Doppler echocardiography in patients 6 months after undergoing successful PCI of the left anterior descending coronary artery. Restenosis of peripheral blood vessels, such as renal or limb arteries may be diagnosed by similar methods, or by functional testing such as treadmill exercise.

In a method of prophylaxis according to the first aspect of the invention that is intended to prevent or reduce development of restenosis, the Annexin A5 or functional analogue or variant thereof is typically administered at the time of or shortly before the intervention aimed at restoring normal blood flow to ischemic tissue. For example, it may be administered at least 1 week, 6 days, 5 days, 4 days, 3 days, 2 days, 1 day, 12 hours, 8 hours, 4 hours, 2 hours, 1 hour or 30 minutes before the intervention or at the time of the intervention. Typically, administration of the Annexin A5 or functional analogue or variant thereof is continued after the surgical intervention, for example for at least 1 week, 2 weeks, 1 month, 2 months, 6 months, 1 year, 2 years, 5 years or 10 years after the intervention. Annexin A5 or functional analogue or variant thereof may be provided by repeat administration of suitable dosage forms, or by administration in a controlled release form, such as in a drug eluting stent deployed during the intervention, or as a combination of one or more forms of administration. It will be appreciated that the exact duration of continuation of administration of the Annexin A5 or functional analogue or variant thereof may be chosen to coincide with the degree of risk of restenosis at different times after the intervention. For example, where a bare-metal stent is deployed during the intervention, neointima formation typically peaks at about 6 months after the intervention, and then regresses, whereas where a drug eluting stent is deployed, restenosis tends to develop more slowly, but continues to develop up to 1 or 2 years or even more than 2 years after intervention (Ong and Serruys (2005) *Curr Issues Cardiol* 32: 372-377).

In other embodiments of the first aspect of the invention, Annexin A5 or functional analogue or variant thereof is administered as a secondary prophylaxis, to prevent or reduce worsening of restenosis that has already occurred; or as a treatment, to completely or partially reverse restenosis that has already occurred. Typically, the Annexin A5 or functional analogue or variant thereof is administered after the primary revascularisation procedure, and following diagnosis of restenosis in the patient. Typically, Annexin A5 or functional analogue or variant thereof is provided by repeat administration of suitable dosage forms. Typically, administration is continued for at least 1 week, 2 weeks, 1 month, 2 months, 6 months, 1 year, 2 years, 5 years or 10 years after diagnosis of restenosis. It is also envisaged that a further revascularisation procedure may be undertaken as a treatment for the restenosis, and that the Annexin A5 or functional analogue or variant thereof may be provided as a controlled release drug, such as in a drug eluting stent deployed during the further revascularisation procedure. A combination of one or more forms of administration may be provided.

By administering a "therapeutically effective amount of Annexin A5 or a functional analogue or variant thereof", we mean administering an amount which has a beneficial effect in preventing or reducing the development of restenosis, treating restenosis, or preventing or reducing the worsening of existing restenosis. Where the Annexin A5 or a functional analogue or variant thereof prevents or reduces development of restenosis, typically, restenosis is not diagnosable following onset of administration, or it becomes diagnosable later than would be expected (i.e. compared to its development in the absence of the administration of Annexin A5 or functional analogue or variant thereof), or develops less quickly after diagnosis, or develops to a reduced extent after diagnosis, or there is a combination of any two or all three of later diagnosability, slower progression and reduced development. Typically, restenosis would be diagnosable at least 1 month, at least 3 months, 6 months, 1 year, 2 years, 5 years or 10 years later than would have been expected in the absence of administration of Annexin A5 or a functional analogue or variant thereof. Where, following diagnosis of restenosis, progression of restenosis is slower in the patient who has been administered the Annexin A5 or a functional analogue or variant thereof, this typically results in the need for a repeat revascularisation procedure to occur later, typically, at least 1 month, at least 3 months, 6 months, 1 year, 2 years, 5 years or 10 years later than would have been expected in the absence of administration of Annexin A5 or a functional analogue or variant thereof. Typically, where the Annexin A5 or a functional analogue or variant thereof is administered to treat restenosis, symptoms of restenosis disappear over time, such that restenosis is no longer diagnosable at 10 years, at 5 years, 2 years, 1 year, 6 months, 3 months or at 1 month following administration. Where Annexin A5 or a functional analogue or variant thereof is administered to prevent or reduce the worsening of existing restenosis, this typically results in the need for a repeat revascularisation procedure to occur later, typically, at least 1 month, at least 3 months, 6 months, 1 year, 2 years, 5 years or 10 years later than would have been expected in the absence of administration of Annexin A5 or a functional analogue or variant thereof.

Suitably, the beneficial effect of administering Annexin A5 or a functional analogue or variant thereof on restenosis (e.g. later diagnosability, slower progression and/or reduced development) can be identified by determining by IVUS the mean lumen diameter or mean lumen area of the blood vessel that is at risk of or has undergone restenosis following a revascularisation procedure, in a subject who has been and/or is being administered Annexin A5 or a functional analogue or variant thereof, and comparing it to the same parameter in a subject who has undergone the same type of revascularisation procedure in the same type of blood vessel a similar period of time ago, but who has not be administered Annexin A5 or a functional analogue or variant thereof. Suitably, the mean lumen diameter will be at least 1%, 2%, 3%, 4%, 5%, 7%, 10%, 15%, 20%, 25%, 30%, 40%, 50%, 75%, 100%, 125%, 150% or even 200% larger in the treated subject than in the subject who has not been treated with Annexin A5 or a functional analogue or variant thereof, at a time point of 1 week, 2 weeks, 1 month, 2 months, 4 months, 6 months, 9 months, 1 year, 2 years, 5 years or 10 years after the revascularisation procedure has been performed, assuming that administration of Annexin A5 or a functional analogue or variant thereof was commenced at the time of or before the revascularisation procedure. Alternatively, the mean lumen area will typically be at least 2%, 3%, 4%, 5%, 7%, 10%, 15%, 20%, 45%, 55%, 70%, 100%, 225%, 300%, 400%, 500%, 600% or even 900% larger in the treated than the untreated subject at any of the time points mentioned above. Preferably, the above noted increase in mean lumen diameter or area is observed at 6 months after the revascularisation procedure.

The skilled person will appreciate that other endpoints may be appropriate to identify a therapeutic effect of administration of Annexin A5 or functional analogue or variant thereof. For example, myocardial infarction and/or death are common consequences of restenosis. Subjects administered Annexin A5 or functional analogue or variant thereof may experience a reduced risk of myocardial infarction, and/or survive for longer than would be expected in the absence of the administration of Annexin A5 or functional analogue or variant thereof.

An effect of administration of Annexin A5 or a functional analogue or variant thereof on diagnosability of restenosis following a revascularisation procedure can be determined by clinical trials, typically involving tens, hundreds, or thousands of patients (such as 10, 50, 100, 1000 or 10000 or values between these). Alternatively, animal tests may be used, such as those described below in relation to the testing of functional analogues and variants of Annexin A5, and in the Examples.

Subjects who may benefit from prophylaxis or treatment according to the first aspect of the invention include subjects who are to undergo an intervention aimed at restoring normal blood flow to ischemic tissue, or those subjects at the time of the intervention or subsequent to the intervention. The patient can be a subject undergoing or having undergone a revascularisation procedure in the coronary circulation or in a peripheral vessel. Such an intervention may be a surgical intervention or a percutaneous intervention. For example, the procedure can be a bypass grafting, such as coronary artery bypass grafting, or a catheter based intervention, such as balloon angioplasty with or without implantation of a stent and with or without atherectomy, such as percutaneous coronary intervention or angioplasty. Suitably, in the first aspect of the invention, the restenosis is associated to a bypass grafting. In other words, the restenosis has occurred, or is at risk of occurring, due to a bypass grafting procedure. Suitably, in the first aspect of the invention, the restenosis is associated to a catheter based intervention. In other words, the restenosis has occurred, or is at risk of occurring, due to a catheter based intervention. Suitably, the restenosis is associated with the implantation of a stent, whether or not this procedure has been performed in the context of a surgical intervention such as bypass grafting, or a catheter based intervention. Other suitable subjects include subjects who have been or are to be treated for an aneurysm, such as by stent grafting.

The Annexin A5 or the functional analogue or variant thereof can be administered in conjunction with one or more further active agent(s), such as a thrombolytic therapeutic such as aspirin, clopidogrel, triclopidine, tissue plasminogen activator, urokinase, or a bacterial enzyme such as streptokinase. The Annexin A5 or functional analogue or variant thereof can be co-administered with any of one or more further active agent(s), or it may be administered separately, simultaneously or sequentially with such agent(s). Typically, one or more of these agents is used to reduce the risk of thrombosis, which can occlude blood vessels, including stented blood vessels. Suitably, therapy is commenced with triclopidine or clopidogrel before a revascularisation procedure involving stent deployment, and is continued for at least three, six or even twelve months after the procedure (Ong and Serruys, supra). Typically, aspirin is administered concomitantly with triclopidine or clopidogrel and then continued indefinitely. The use of aspirin together with clopidogrel or triclopidine is referred to as dual antiplatelet therapy. Similar regimes of antithrombotic drug administration may be applied before and following other types of intervention.

The Annexin A5 or the functional analogue or variant thereof can be administered parenterally, intravenously, intra-arterially, intra-peritoneally, intra-muscularly, subcutaneously or locally from a drug eluting stent. Where a subject has been implanted with a stent, the Annexin A5 or functional analogue or variant thereof may be released from the stent (i.e. the stent is a drug eluting stent) or the subject may be administered Annexin A5 or functional analogue or variant thereof by another of the routes listed above.

In a second aspect, the invention provides a method for the treatment of stenosis in a patient comprising performing an intervention for the treatment of stenosis in conjunction with administering a therapeutically effective amount of Annexin A5 or a functional analogue or variant thereof. Put another way, the second aspect of the invention provides Annexin A5 or a functional analogue or variant thereof for use in the treatment of stenosis in conjunction with a stenosis therapy.

Stenosis may occur and may be diagnosed as described above. By "an intervention for the treatment of stenosis" we mean any intervention intended to treat stenosis in a patient. Art known stenosis interventions include surgical interventions, such as vein grafting, including bypass grafting such as coronary artery bypass grafting, and catheter-based interventions, such as balloon angioplasty with or without implantation of a stent and with or without atherectomy, including percutaneous coronary intervention.

In the second aspect of the invention, the Annexin A5 or functional analogue or variant thereof is administered in conjunction with the intervention for the treatment of stenosis. In other words, the administration and the intervention are performed separately, simultaneously or sequentially. As discussed in relation to the first aspect of the invention, the Annexin A5 or functional analogue or variant thereof may be administered at least 1 week, 6 days, 5 days, 4 days, 3 days, 2 days, 1 day, 12 hours, 8 hours, 4 hours, 2 hours, 1 hour or 30 minutes before the intervention or at the time of the intervention. Typically, administration of the Annexin A5 or functional analogue or variant thereof is continued after the surgical intervention, for example for at least 1 week, 2 weeks, 1 month, 2 months, 6 months, 1 year, 2 years, 5 years or 10 years after the intervention.

The Annexin A5 or functional analogue or variant thereof is administered in order to prevent or reduce the development of restenosis following the stenosis treatment. Thus a "therapeutically effective amount" of Annexin A5 or functional analogue or variant thereof has a beneficial effect in preventing or reducing the development of restenosis, as described above in relation to the first aspect of the invention.

Suitable subjects and patient groups who may benefit from the method of the second aspect of the invention, suitable routes and doses of administration, and suitable adjunct therapies, are as described above in relation to the first aspect of the invention.

A third aspect of the invention provides a pharmaceutical composition comprising a therapeutically effective amount of Annexin A5 or a functional analogue or variant thereof for the prophylaxis or treatment of restenosis. Put another way, the third aspect of the invention provides use of Annexin A5 or a functional analogue or variant thereof for the manufacture of a medicinal product for the prophylaxis or treatment of restenosis.

Prophylaxis and treatment of restenosis are as described in relation to the first aspect of the invention.

A pharmaceutical composition according to the third aspect of the invention may thus comprise Annexin A5 or a functional analogue or variant thereof in admixture with a pharmaceutically or veterinarily acceptable adjuvant, diluent or carrier, which will typically be selected with regard to the intended route of administration and standard pharmaceutical practice. The composition may be in the form of immediate-, delayed- or controlled-release applications. Preferably, the formulation is a unit dosage containing a daily dose or unit, daily sub-dose or an appropriate fraction thereof, of the active ingredient.

The phrases "pharmaceutical or pharmacologically acceptable" refer to compositions that do not produce an adverse, allergic or other untoward reaction, when administered to an animal, such as, for example, a human, as appropriate. The preparation of such pharmaceutical compositions are known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, salts, preservatives, drugs, drug stabilizers, excipients, disintegration agents, such like materials and combinations thereof, as would be known to one of ordinary skill in the art. Except insofar as any conventional carrier is incompatible with the active ingredient, its use in the therapeutic or pharmaceutical compositions is contemplated.

The pharmaceutical compositions according to the invention may, or may not, be intended for, and, thus formulated in a manner suitable for, parenteral, intravenous, intra-arterial, intraperitoneal, intra-muscular or subcutaneous administration, or administration from a drug-eluting stent, or they may be administered by infusion techniques. Sterile injectable solutions may be prepared by incorporating the active compounds in the required amount in the appropriate solvent with various of the other ingredients enumerated above, as required, followed by sterilization. The pharmaceutical compositions may be best used in the form of a sterile aqueous solution which may contain other substances, for example, enough salts or glucose to make the solution isotonic with blood. The aqueous solutions may be suitably buffered (preferably to a pH of from 3 to 9), if necessary. The preparation of suitable pharmaceutical formulations under sterile conditions is readily accomplished by standard pharmaceutical techniques well-known to those skilled in the art.

A therapeutically effective amount of Annexin A5 or a functional analogue or variant thereof for administration to a patient, such as a human patient, on the basis of a daily dosage level may be from 0.01 to 1000 mg of Annexin A5 or a functional analogue or variant thereof per adult (for example, from about 0.001 to 20 mg per kg of the patient's body weight, such as 0.01 to 10 mg/kg, for example greater than 0.1 mg/kg and less than 20, 10, 5, 4, 3 or 2 mg/kg, such as about 1 mg/kg), administered in single or divided doses. Suitable doses to include in drug eluting stents are discussed below in relation to the fourth aspect of the invention.

The physician in any event will determine the actual dosage which will be most suitable for any individual patient and it will vary with the age, weight and response of the particular patient. The above dosages are exemplary of the average case.

There can, of course, be individual instances where higher or lower dosage ranges are merited and such are within the scope of this invention.

For veterinary use, a compound of the invention is administered as a suitably acceptable formulation in accordance with normal veterinary practice and the veterinary surgeon will determine the dosing regimen and route of administration which will be most appropriate for a particular animal.

A fourth aspect of the invention provides a drug eluting stent, wherein the drug is Annexin A5 or a functional analogue or variant thereof.

A stent is a scaffold used to maintain a blood vessel in an open position, and is typically deployed during catheter based interventions. Drug eluting stents contain, in addition to a stent body, at least a drug and typically also a coating which allows for controlled elution of the drug. Typical stent bodies are at least partly flexible or articulated (i.e., adjacent expansible ring segments are connected by links that articulate relative to one another) over their lengths so that they may be advanced through the vasculature. Further they should have sufficient mechanical strength after they are expanded, in order to mechanically augment the luminal wall strength and thus maintain lumen patency. Stent bodies are typically tube-shaped and have a mesh structure. Suitable stent bodies are disclosed in U.S. Pat. No. 6,602,282 (Assignee Avantec Vascular Corporation). Stents having expansible ring segments joined by sigmoidal links and axial beams are described in WO 99/17680 (Localmed Inc). Stents comprising expansible rings including struts and hinges where the hinges are configured to have different opening forces are described in U.S. Pat. No. 5,922,020 (Localmed Inc). Typical stents will have a length in the range from about 5 mm to 100 mm, usually being from about 8 mm to 50 mm. The small (radially collapsed) diameter of cylindrical stents will usually be in the range from about 0.5 mm to 10 mm, more usually being in the range from 0.8 mm to 1.25 mm. The expanded diameter will usually be in the range from about 1.5 mm to 50 mm, preferably being in the range from about 2.5 mm to 30 mm.

The stent body can be manufactured from any suitable material, including stainless steel, titanium, nickel or alloys, such as cobalt chrome alloys, or combinations thereof. Particularly suitable materials include malleable metals, such as 300 series stainless steel, or resilient metals, such as superelastic and shape memory alloys, e.g., Nitinol® alloys, spring stainless steels, and the like. It is possible that the body segments could be formed from combinations of these metals, or combinations of these types of metals and other non-metallic materials. Stent bodies may also be made of a bioresorbable or biodegradable material. A suitable biodegradable stent body is made from a polyester such as polylactide as described in Vogt et al (2004) *European Heart Journal* 25: 1330-40. This stent body was used as the platform for eluting paclitaxel, which it was able to do over a period of more than two months from deployment.

The Annexin A5 or the functional analogue or variant thereof is incorporated onto or into the stent body by a method suitable to allow for its gradual release following deployment of the stent.

Blindt et al (1999) *Int J Artif Organs* 22: 843-853 describe a method of molding stents from bioresorbable polymers such as poly-D-L-lactide, which they call CESP (controlled expansion of saturated polymers). The CESP process is characterised by the exposure of an amorphous polymer to an inert gas at high pressure, such as carbon dioxide, which has a plasticizing effect, making it possible to process polylactides at a temperature close to room temperature. The low process temperature constitutes a key advantage for thermally sensitive polymers and allows the incorporation of thermally sensitive pharmaceutical additives during the molding process. Drug release kinetics can be regulated by different pore sizes of the material. The CESP method was used Vogt et al, supra to make a poly-D-L-lactide paclitaxel eluting stent.

Annexin A5 or the functional analogue or variant thereof may also be incorporated onto the stent body by coating the stent body after it has been formed. In this embodiment, the stent body is coated with the Annexin A5 or the functional analogue or variant thereof and typically also a further material, such as a polymer suitable to allow slow release of the Annexin A5 or the functional analogue or variant thereof. Typically, in this embodiment, the stent body comprises a metal, as described above. However, a coating may also be applied in the case of bioerodible or biodegradable stent bodies, even if these also include Annexin A5 or functional analogue or variant thereof incorporated at the molding stage.

Suitably, where the stent body is coated, there is at least one, two, three or more coatings. US 2006/0083772 (DeWitt et al) describes suitable coating compositions and their use in applying a bioactive agent to a surface of an implantable medical device, such as a stent, in a manner that will permit the bioactive agent to be released from the coating in vivo. The composition comprises a plurality of compatible polymers having different properties that can permit them to be combined together to provide an optimal combination of such properties as durability, biocompatibility and release kinetics. The coating composition described in US 2006/0083772 comprises one or more bioactive agents in combination with a plurality of polymers, including: (a) a first polymer component comprising a polymer selected from the group consisting of (i) ethylene copolymers with other alkylenes, (ii) polybutenes, (iii) aromatic group-containing copolymers, (iv) epichlorohydrin-containing polymers, (v) poly(alkylene-co-alkyl(meth)acrylates), and (vi) diolefin-derived, non-aromatic polymers and copolymers; and (b) a second polymer component comprising one or more polymers selected from the group consisting of poly(alkyl(meth)acrylates) and poly(aromatic(meth)acrylates), where "(meth)" includes such molecules in either the acrylic and/or methacrylic form (corresponding to the acrylates and/or methacrylates, respectively). Criteria for selection of polymers and in vitro tests for determining release rate of an active agent are also disclosed in US 2006/0083772. Furthermore, US 2006/0083772 discloses pre-treatment of stents by coating with materials such as silane and/or a polymer of the low-molecular-weight dimer of para-chloro-xylylene (Parylene™ C; Speciality Coating Systems (Indianapolis)), in order to improve adherence of subsequent polymer layers. A top-coat layer may also be included, to improve biocompatibility, protect against delamination, and/or to reduce initial drug elution rates to provide for longer elution times.

US2005/0037052 (Medtronic Vascular, Inc.) discloses drug eluting stents having coatings of between 1 μm and 1000 μm thickness. In one configuration the drug-containing coating is applied directly to the device surface or onto a polymer primer coat such a parylene. Depending on the solubility rate and profile desired, the drug is either entirely soluble within the polymer matrix, or evenly dispersed throughout. The drug concentration present in the polymer matrix ranges from 0.1% by weight to 80% by weight. In another configuration, a drug-free polymer barrier, or cap coat is applied over the drug-containing coating. The drug-containing coating serves as a drug reservoir. Generally, the concentration of drug present in the reservoir ranges from about 0.1% by weight to as much as 100%. The barrier coating participates in controlling drug release rates in at least three ways. Firstly, if the barrier coat has a solubility constant different from the underlying drug-containing coating, the drug's diffusivity through the barrier coat is regulated as a function of the barrier coating's solubility factors. The more miscible the drug is in the barrier coat, the quicker it will elute form the device surface and visa versa. This coating configuration is commonly referred to as a reservoir coating. Secondly, the barrier coat may comprise a porous network where the coating acts as a molecular sieve. The larger the pores relative to the size of the drug, the faster the drug will elute. Moreover, intramolecular interactions will also determine the elution rates. Finally, while coating thickness is generally a minor factor in determining overall drug-release rates and profile, it is nevertheless an additional factor that can be used to tune the coatings. Basically, if all other physical and chemical factors remain unchanged, the rate at which a given drug diffuses through a given coating is inversely proportional to the coating thickness. It is possible to use the controlled release coatings described in US2005/0037052 with a cap coat. For example, US2005/0037052 discloses a metal stent having a parylene primer coat applied to its bare metal surface. Over the primer coat a drug-releasing polymer coating or blend of polymers is applied. Over the drug-containing coating a polymer cap coat is applied. The cap coat may optionally serve as a diffusion barrier to further control the drug release, or provide a separate drug. The cap coat may be merely a biocompatible polymer applied to the surface of the stent to protect the stent and have no effect on elusion rates. US2005/0037052 also discloses methods for coating a stent with the various polymer compositions.

Where a polymer is used in the coating, it may be a durable polymer or a biodegradable polymer. the polymer can be selected from polyurethanes, polyethylene terephthalate, PLLA-poly-glycolic acid (PGA) copolymer (PLGA), polycaprolactone, polyalkanoate polymers and copolymers such as poly-(hydroxybutyrate/hydroxyvalerate) copolymer, poly (vinylpyrrolidone), polytetrafluoroethylene, poly(2-hydroxyethyl methacrylate), poly(etherurethane urea), silicones, acrylics, epoxides, polyesters, urethanes, parlenes, polyphosphazene polymers, fluoropolymers, polyamides, polyolefins, and mixtures thereof.

The stent can further be coated with a layer of an antithrombotic material comprising or consisting of one or more agents selected from polysaccharides, heparin, gelatin, collagen, alginate, hyalunic acid, alginic acid, carrageenan, chondroitin, pectin, chitosan, and their derivatives and copolymers. Suitably, these agents can be incorporated in a biocompatible topcoat, as described in US 2006/0083772.

Suitable drug-eluting stents may be made using the coating methods and materials described above. In vitro tests may be performed to assess drug release profiles in aqueous media, as described in US2005/0037052 and US 2006/0083772. Suitably, a drug eluting stent according to the fourth aspect of the invention should release the Annexin A5 or functional analogue or variant thereof over a period of at least 1 day, at least 2 days, at least 3 days, at least 5 days, 10 days, 20 days, 30 days, 40 days, 50 days, 60 days, 70 days, 80 days, 90 days or even 100 or 150 days following deployment. Suitably, no more than 60%, 70%, 80% or 90% is released in the first third of the period over which the stent releases the Annexin A5 or functional analogue or variant thereof.

A suitable quantity of Annexin A5 or functional analogue or variant thereof may be in the range of about one microgram to about 10 milligram (mg) of bioactive agent per $cm^2$ of the effective surface area of the device, and typically between about 5 μg and about 10 mg, more typically between about 1 μg and about 1 mg. In Vogt et al, supra, the stent had a surface area of 87 $mm^2$ and contained 170 μg of paclitaxel.

A fifth aspect of the invention provides a method for making a stent for delivering Annexin A5 or a functional analogue or variant thereof to a patient, comprising incorporating Annexin A5 or a functional analogue or variant thereof into or onto a stent body. Methods suitable for incorporating a drug into or onto a stent body are described in Blindt et al (1999) *Int J Artif Organs* 22: 843-853, US2005/0037052 and US 2006/0083772.

In a preferred embodiment of the fifth aspect of the invention, the method comprises a) providing a stent body having a surface, and b) applying a coating over at least a portion of said surface, wherein said coating comprises Annexin A5 or a functional analogue or variant thereof. Suitably, the luminal surface, or the transluminal surface or both surfaces are coated. Methods of coating a stent body, and suitable coating compositions are described in US2005/0037052 and US 2006/0083772. Art-known methods such as dipping, spraying, ultrasonic- or vacuum-deposition may be employed to apply a coating of a solution of a material in a suitable solvent. US2005/0037052 describes that a porosity gradient in the coating can be attained by phase separation, such as by addition of a non-solvent to the polymer solution. The higher the amount of non-solvent, the higher the degree of phase separation and the higher the porosity in the film. The coat next to the stent surface may be formulated with the highest amount of non-solvent to exhibit the most porosity. Successive coats of drug-polymer solutions may then be formulated with decreasing amounts of non-solvent which will provide a coating system with progressively lower porosity.

In another embodiment of the fifth aspect of the invention, the method comprises molding a stent from a composition comprising a polymer and Annexin A5 or a functional analogue or variant thereof. A method of molding a stent from a mixture of a polymer and a drug compound is disclosed in Blindt et al (1999) *Int J Artif Organs* 22: 843-853.

The Annexin A5 or functional analogue or variant thereof referred to in relation to any of the first to fifth aspects of the invention may be selected from:
a) human Annexin A5 (SEQ ID NO:1);
b) a mammalian orthologue of human Annexin A5;
c) an allelic or genetic variant of a) or b);
d) a functional analogue of Annexin which is a protein which is more than 50%, 60%, 70%, 75%, such as more than 80%, 85%, more than 90%, or even more preferably more than 95% or 99% identical to human Annexin A5, SEQ ID NO:1;
e) a dimer of, or fusion protein comprising, any of a), b), c) or d); and
f) a PEGylated variant of any of a), b), c), d) or e).

In particular embodiments, the functional analogue or variant of Annexin A5 according to the invention is more than 50%, 60%, 70%, 75%, such as more than 80%, 85%, more than 90%, or even more preferably more than 95% or 99% identical to human Annexin A5, SEQ ID NO:1.

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.b<t); -p is set to blastp; -o is set to any desired file name (e.g., C:\output.txt); and all other options are left at their default setting. For example, the following command can be used to generate an output file containing a comparison between two amino acid sequences: C:\BI2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:1 (the length of the sequence set forth in SEQ ID NO:1 is 320) and the number of matches is 288, then the sequence has a percent identity of 90 (i.e., 288÷320*100=90) to the sequence set forth in SEQ ID NO:1.

Thus, a functional analogue or variant of Annexin A5 may be a protein wherein at one or more positions there have been amino acid insertions, deletions, or substitutions, either conservative or non-conservative, provided that such changes result in a protein whose basic properties to function in an equivalent manner to Annexin A5 have not significantly been changed. "Significantly" in this context means that one skilled in the art would say that the properties of the variant may still be different but would not be unobvious over the ones of the original protein.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the methods of protein engineering and site-directed mutagenesis which are well known in the art.

The functional analogue or variant of Annexin A5 according to the invention may be a dimer of Annexin A5 (such as DiAnnexin A5) or a functional analogue or variant thereof, or may be a PEGylated Annexin A5 or a functional analogue or variant thereof. DiAnnexinA5 and PEGylated AnnexinA5 are disclosed in WO 02/067857.

PEGylation is a method well known to those skilled in the art wherein a polypeptide or peptidomimetic compound (for the purposes of the present invention, Annexin A5 or the functional analogue or variant) is modified such that one or more polyethylene glycol (PEG) molecules are covalently attached to the side chain of one or more amino acids or derivatives thereof. It is one of the most important molecule altering structural chemistry techniques (MASC). Other MASC techniques may be used; such techniques may improve the pharmacodynamic properties of the molecule, for example extending its half life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., (2001), Biodrugs 15, 419-429). Methods that may be used to covalently attach the PEG molecules to polypeptides are further described in Roberts et al., (2002) Adv Drug Deliv Rev, 54, 459-476, Bhadra et al., (2002) Pharmazie 57, 5-29, Kozlowski et al., (2001) J Control Release 72, 217-224, and Veronese (2001) Biomaterials 22, 405-417 and references referred to therein.

The advantages of PEGylation to the polypeptide or peptidomimetic compound of the invention include reduced renal clearance which, for some products, results in a more sustained adsorption after administration as well as restricted distribution, possibly leading to a more constant and sustained plasma concentrations and hence an increase in clinical effectiveness (Harris et al., (2001) Clin Pharmacokinet 40, 539-551). Further advantages can include reduced immunogenicity of the therapeutic compound (Reddy, (2001) Ann Pharmacother 34, 915-923), and lower toxicity (Kozlowski et al., (2001), Biodrugs 15, 419-429).

The functional analogue or variant of Annexin A5 can be a fusion protein comprising the sequence of Annexin A5 or a variant thereof. Thus, for example, Annexin A5 or a variant thereof can be fused to one or more fusion partner polypeptide sequence(s) so as to extend the half-life of the molecule within a patient's circulatory system and/or add further functionality to the molecule.

A "functional" analogue or variant of Annexin A5 may be capable of binding to phosphatidylserine on a biological membrane, preferably to a level that is at least 10%, 20%, 30%, 40%, 50%, 60%, 70%, 80%, 90%, 95%, 99% or about 100% of that displayed by human Annexin A5 (SEQ ID NO:1) under the same conditions. A suitable method for measuring Annexin A5 binding to phosphatidylserine on a biological membrane is known in the art (Vermes, I., et al., *A novel assay for apoptosis. Flow cytometric detection of phosphatidylserine expression on early apoptotic cells using fluorescein labelled Annexin V*. J Immunol Methods, 1995. 184 (1): p. 39-51).

A "functional" analogue or variant of Annexin A5 may, additionally, or alternatively, possess at least 10%, 20%, 30%, 40%, 50%, 60%, 70%, 80%, 90%, 95%, 99% or about 100% of the therapeutic activity human AnnexinA5 (SEQ ID NO:1) when used at the same (i.e. molar equivalent) dosage, for prophylaxis or treatment of restenosis in accordance with the first aspect of the invention. In this context, the therapeutic activity of a "functional" analogue or variant of Annexin A5 may be determined, compared to that of human Annexin A5 (SEQ ID NO:1), by comparing the ability of a molar equivalent amount of the functional analogue or variant and of human Annexin A5 to treat or provide prophylaxis for restenosis as described above, and/or by animal tests, such as using the methodology set out in the following examples.

One suitable test is as follows: 1. Maintain ApoE*3 Leiden mice on a mildly hypercholesterolemic diet for 3 weeks prior to surgery; 2. one day before surgery and for the remainder of the procedure, treat mice by intraperitoneal injection of 1 mg/kg bw/day of Annexin A5, or a molar equivalent amount of the functional analogue or variant of Annexin A5, or vehicle alone; 3. Cuff the femoral vein with non-constrictive fine bore polyethylene tubing; 4. Sacrifice the mice three days after cuff placement, and examine the vascular composition in the arterial lesion. 5. Compare the results obtained in the mice treated by Annexin A5 with those treated with the functional analogue or variant of Annexin A5, and the untreated mice. Relevant parameters are: the ability of treatment with the Annexin A5 analogue or variant to reduce the percentage of cells attached to endothelium identifiable as leukocytes, compared to the untreated group; the ability of treatment with the Annexin A5 analogue or variant to reduce the percentage of cells in the media identifiable as leukocytes, compared to the untreated group. In either case, the Annexin A5 analogue or variant may have at least 10%, 20%, 30%, 40%, 50%, 60%, 70%, 80%, 90%, 95%, 99% or about 100% of the effect of the Annexin A5 in reducing either or both of these effects.

Another suitable test is as follows: 1. Maintain ApoE*3 Leiden mice on a high fat diet for 3 weeks prior to surgery; 2. One day before surgery, or at the day of surgery, and for the remainder of the procedure, treat mice by intraperitoneal injection of 1 mg/kg bw/day of Annexin A5, or a molar equivalent amount of the functional analogue or variant of Annexin A5, or vehicle alone; 3. Graft the inferior caval vein from a littermate into the common carotid artery; 4. Sacrifice the mice 28 days after vein grafting, and examine the vascular composition and dimensions of the vein graft. 5. Compare the results obtained in the mice treated by Annexin A5 with those treated with the functional analogue or variant of Annexin A5, and the untreated mice. Relevant parameters are: the ability of treatment with the Annexin A5 analogue or variant to reduce the number of leukocytes in the vein graft wall, compared to the untreated group; the ability of treatment with the Annexin A5 analogue or variant to reduce vein graft thickening i.e. neointima area of longitudinal cross-section, compared to the untreated group. In either case, the Annexin A5 analogue or variant may have at least 10%, 20%, 30%, 40%, 50%, 60%, 70%, 80%, 90%, 95%, 99% or about 100% of the effect of the Annexin A5 in reducing either or both of these effects.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Mouse Vein Graft Model

In a mouse model of CABG is a vein graft taken from a donor mouse. In a recipient mouse, a carotid artery is freed from surrounding tissue, and blood flow is stopped by the placement of two artery clamps. The vessel is then sectioned between the two artery clamps, and the vein graft is sutured to fit between the two artery ends. When this procedure is finished, the clamps are removed and blood flow is restored. A detailed description of the method is published (Zou et al., 1998)

When 4 weeks has elapsed, a neointima has formed in the vein graft. The dimension of the neointima is measured histologically after termination of the mice. If the mice used are hyperlipidemic, e.g. apoE (−/−) mice that are given a high fat diet or apoE*3-Leiden mice that are also given a high fat diet, the neointima will develop more rapidly than in normal mice. In such mice, the lesions may reach a so severe state that one can see evidence of endothelial erosion, intraplaque haemorrhage and dissemination, i.e. similar consequences that can happen in patients.

The dimensions of the neointima in mouse vein grafts can be significantly reduced by treatment with Annexin A5. A daily injection of 1 mg Annexin A5/kg bw intraperitoneally will reduce the neointima by at least 20%, showing the efficacy of the treatment.

Example 2

Mouse Perivascular Cuff Model

A cuff placed around the femoral artery of a mouse will lead to the rapid development of a neointima. This model has been used as a model of the neointima formation caused by PCI, and it has been used to evaluate the effects of anti-restenotic drugs (Pires et al., 2006). The neointimal lesions will contain smooth muscle cells, but there will also be recruitment of circulating white cells into the lesions, especially if the procedure is carried out in mice that are hyperlipidemic. The development of the lesions is rapid, and a significant lesion is seen already within 1 week.

The dimensions of the neointima in mouse vein grafts may be significantly reduced by treatment with Annexin A5, and/or the percentage of the total number of cells attached to the endothelium and/or present in the media which are identifiable as leukocytes, such as macrophages, may be significantly decreased. A daily injection of 1 mg Annexin A5/kg bw intraperitoneally may reduce the neointima by at least 20%, showing the efficacy of the treatment.

Summary. An unwanted effect of surgical interventions aiming at restoring normal blood flow to ischaemic tissue is restenosis of the vessel that has been dilated by PCI or in the graft vessels used to bypass the stenosed arterial segment. In animal models of restenosis, it was surprisingly found that Annexin A5 reduced the development of restenosis.

Example 3

Mouse Perivascular Cuff Model—Experimental Results

Balloon angioplasty (with or without stent placement) is a common way to restore blood flow to e.g. ischaemic myocardium in patients with angina pectoris or myocardial infarction. The procedure triggers an inflammation in the dilated vessel segment, which may lead to restenosis, i.e. the dilated vessel segment becomes again stenotic due to the development of a so called neointima. This phenomenon may lead to a need for a repeated vascularisation procedure in as many as 30-50% of the patients within 3-12 months if a stent is not placed in the dilated vessel segment. A bare metal stent can reduce the restenosis rate, but as many as 15-30% may still need revascularisation within 3-12 months.

Placement of a perivascular plastic cuff around the femoral artery in a mouse is an experimental model of an inflammation driven neointima formation, i.e. it is a restenosis model. We tested if annexin A5 could affect neointima formation in this model.

Experimental

Male ApoE*3 Leiden mice were fed a mildly hypercholesterolemic diet for 3 weeks prior to experimental procedure, which continued until the end of the experimental period. One day before surgery the mice were randomized in one of the treatment groups on the basis of plasma cholesterol, triglyceride levels and body weight. Treatment with 1 mg/kg bw/day of annexin A5 (intraperitoneal injection) was started one day before cuff placement and continued daily during the experimental period. At day 0 surgery was performed, i.e. a non-constricting cuff was placed around each femoral artery of the mice. The mice were sacrificed 3 days after the cuff placement.

Surgical Procedure of Cuff Placement

Mice were anesthetized before surgery by intraperitoneal administration of a combination of Midazolam (5 mg/kg, Roche, Woerden, The Netherlands), Medetomidine (0.5 mg/kg, Orion, Espoo, Finland) and Fentanyl (0.05 mg/kg, Janssen, Berchem, Belgium). This cocktail of anaesthetics gives complete narcosis for at least one hour. After shaving the inner side of both legs and disinfecting the surgery area with alcohol (70%) a longitudinal 1 cm incision was made in the internal side of the leg. Next, a 3 mm length of the femoral artery was dissected free from the femoral nerve and femoral vein. The femoral artery was looped with a 6/0 silk ligature (0.7 metric B/BRAUN, Tuttlingen, Germany) for careful manoeuvring of the artery. A non-constrictive fine bore polyethylene tubing (Portex, Kent, UK; 0.40 mm inner diameter, 0.80 mm outer diameter and an approximate length of 2 mm) was longitudinally opened and sleeved loosely around the femoral artery. The cuff was closed up with two 6/0 silk ligature knots. The skin was closed with a continued suture. After surgery, anaesthesia was antagonized subcutaneously with Atipamezol and Flumazenil. Animals were placed in a clean cage on top of a heating pad for at least 4 hours.

Sacrifice of the Animals

For histological analysis, animals were sacrificed 3 days after cuff placement. After anaesthesia (Midazolam/Medetomidine/Fentanyl) and blood sampling, the thorax was opened and a mild pressure-perfusion (100 mmHg) with 3.7% formaldehyde in phosphate buffered saline (PBS) (wt/vol) was performed for 5 minutes by cardiac puncture in the left ventricle. After perfusion, the cuffed femoral artery was harvested, fixed overnight in 3.7% formaldehyde in PBS (wt/vol) and paraffin-embedded. Serial cross sections (5-µm thick) were taken from the entire length of the cuffed femoral artery segment for histological analysis.

Blood Sampling

Blood was collected in $K_2$EDTA capillary tubes (Microvette, Sarstedt, Germany) from the tail (one day before surgery for randomization) or by caval vein (sacrifice). Capillary tubes were kept cool at 4° C. for half an hour followed by centrifugation at 6000 RPM (1200 G) for 10 minutes in a cooled 4° C. centrifuge. Plasma was subsequently aliquoted for further analysis. At sacrifice, the plasma was aliquoted in 1.5 ml polypropylene tubes (Eppendorf), one sample of 20 µl for cholesterol and triglyceride analysis and the remaining plasma for reserve analysis. Samples were stored at −80° C.

Cholesterol and total triglycerides levels were determined in the plasma samples taken one day before surgery and at sacrifice. Total plasma cholesterol was measured enzymatically with kit 1489437 (Roche Diagnostics, Almere, The Netherlands) and total triglyceride concentrations were measured with kit 148872 (Roche Diagnostics, Almere, The Netherlands).

Vascular Composition

The vascular composition was analyzed by immunocytochemistry and histomorphometric analysis with regard to the number of leukocytes (anti-CD45 antibodies dilution 1:200, Pharmingen, San Diego, USA), monocytes and macrophages (AIA 31240 macrophage staining dilution 1:3000, Accurate Chemical, Wesbury, USA) and cells expressing tumor necrosis factor alpha (tumor necrosis factor alpha staining dilution 1:200, BioLegend, San Diego, Calif., USA) and monocyte chemotactic protein-1 (monocyte chemotactic protein-1 staining dilution 1:100, Santa Cruz Biotechnology, Inc., Santa Cruz, Calif., USA) in the cuffed femoral arteries.

Results

Vascular Composition of Cuffed Femoral Artery Lesions

Figure 1:
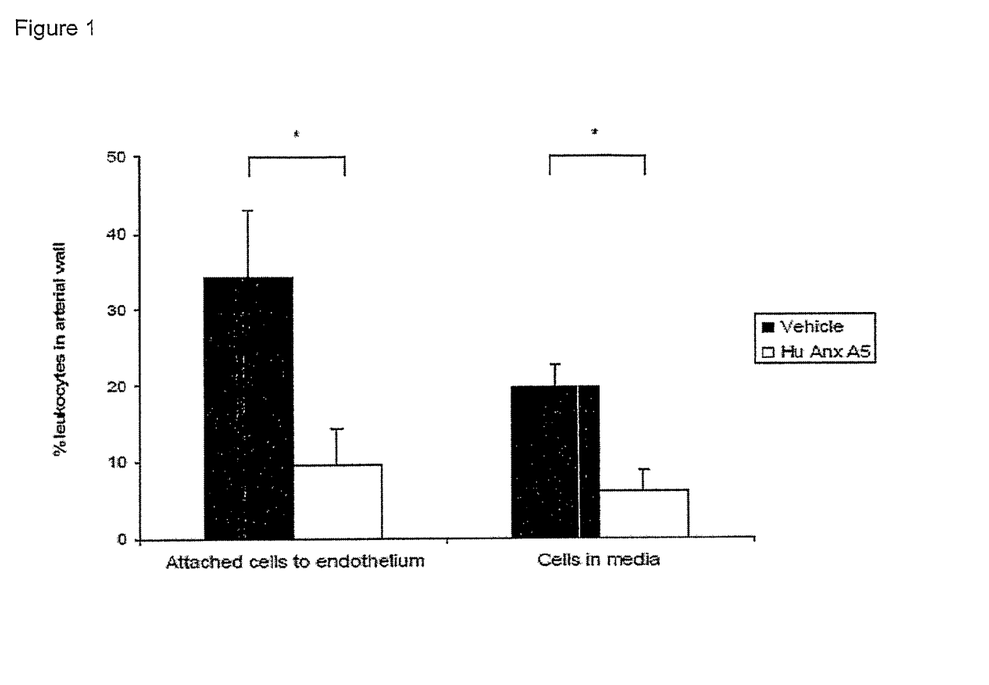
FIG. 1. Quantification of leukocytes the arterial wall in APOE*3-Leiden transgenic mice, fed a cholesterol-rich diet, three days after femoral artery cuff surgery and daily treatment with vehicle or recombinant human annexin A5. The percentage of leukocytes is expressed as mean±SEM.

The percentage of the total number of cells attached to the endothelium identified as leukocytes was significantly decreased by 71.3% (p=0.015) to 9.69±8.9% in the recombinant human annexin A5 treated group in comparison to the vehicle group (34.2±3.0%). The percentage of the total number of cells in the media identified as leukocytes was significantly decreased by 69.0% (p=0.031) to 6.1±2.6% in the recombinant human annexin A5 treated group in comparison to the vehicle group (19.55±4.6%) (FIG. 1).

Monocytes and Macrophages

Figure 2:
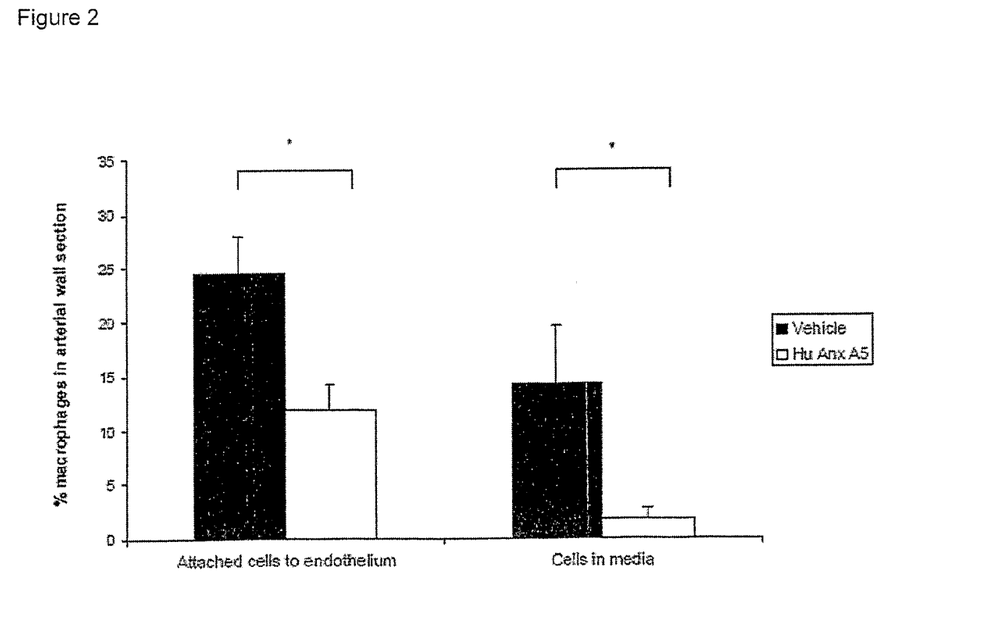
FIG. 2. Quantification of monocytes and macrophages stained with AIA 31240 in the arterial wall in APOE*3-Leiden transgenic mice, fed a cholesterol-rich diet, three days after femoral artery cuff surgery and daily treatment with vehicle or recombinant human annexin A5. The percentage of macrophages in the total number of cells counted (attached to the endothelium or infiltrated in the media) is expressed as mean±SEM.

The percentage of the total number of cells attached to the endothelium identified as macrophages was significantly decreased by 51.4% (p=0.014) to 11.9±2.3% in the recombinant human annexin A5 treated group in comparison to the vehicle group (24.5±3.5%). The percentage of the total number of cells in the media identified as macrophages was significantly decreased by 87.3% (p=0.018) to 1.8±0.9% in the recombinant human annexin A5 treated group in comparison to the vehicle group (14.2±5.5%) (FIG. 2).

Figure 3:
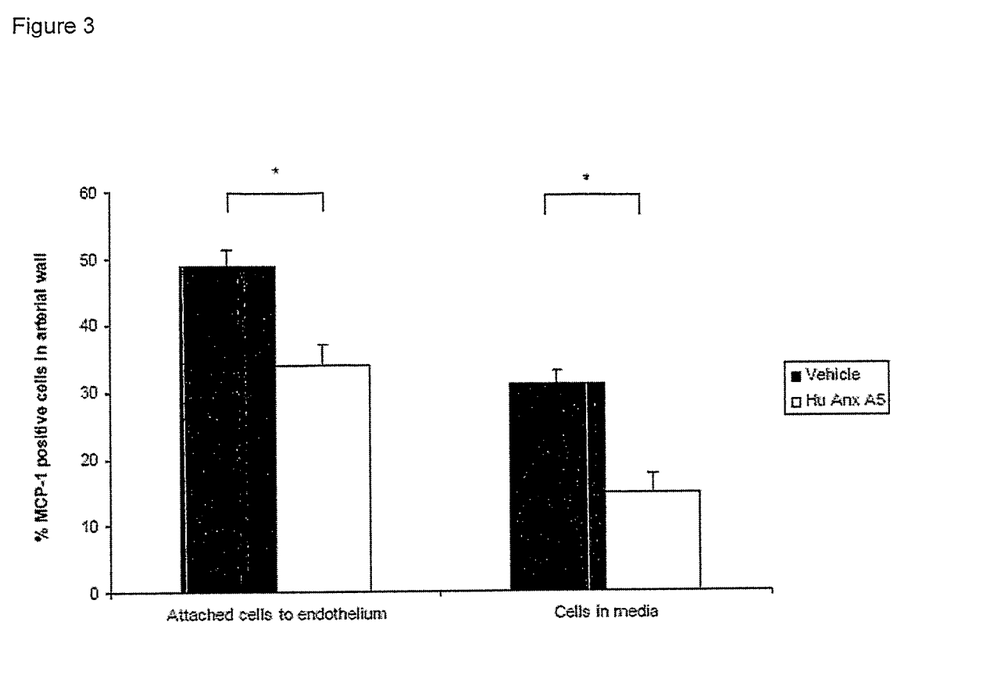
FIG. 3. Quantification of cells expressing MCP-1 in the arterial wall in APOE*3-Leiden transgenic mice, fed a cholesterol-rich diet, three days after femoral artery cuff surgery and daily treatment with vehicle or recombinant human annexin A5. The percentage of cells expressing MCP-1 is expressed as mean±SEM.

The percentage of the total number of cells attached to the endothelium identified as cells expressing MCP-1 such as inflammatory cells and SMCs was significantly decreased by 31.0% (p=0.003) to 33.9±3.1% in the recombinant human annexin A5 treated group in comparison to the vehicle group (49.1±2.2%). The percentage of the total number of cells in the media identified as cells expressing MCP-1 was significantly decreased by 52.7% (p=0.001) to 14.7±2.8% in the recombinant human annexin A5 treated group in comparison to the vehicle group (31.1±1.8%) (FIG. 3). The number of cells expressing TNFα was also significantly reduced in the treatment group as compared to the control group.

Conclusion

These experiments demonstrate clearly the anti-inflammatory effects of annexin A5 in this model of inflammation driven vascular disease. Inflammation (measured as accumulation of leucocytes in the vessel wall) was markedly inhibited by annexin A5 treatment. Furthermore, annexin A5 could also significantly reduce the number of inflammatory cells that were activated, as fewer cells were staining positive for the pro-inflammatory cytokine MCP-1. The results strongly support that annexin A5 is an effective treatment for the prevention of restenosis following balloon angioplasty (with or without stent placement)

Example 4

Mouse Vein Graft Model—Experimental Results

Vein grafting, the bypassing of a stenosed vascular segment, is a method to restore blood flow to an organ that has become ischaemic. The most common application is the placement of a so called coronary artery bypass graft (CABG). Today this procedure is common to restore blood flow to ischaemic myocardium in patients where the location of the stenosis is not suitable for catheter based intervention. When a vein graft is placed in the arterial circulation, its morphology will adopt to the higher blood pressure and blood flow rates in the arterial circulation. Although this procedure is effective, and has rescued many individuals with coronary heart disease, it is associated with a risk of restenosis, a process where the grafted vein develops a neointima that will obstruct blood flow. We investigated if annexin A5 can affect neointima formation in a mouse model of CABG. In this experiment, which had a duration of 28 days, we used both human and murine annexin A5. This is because a human protein may give rise to a non-specific immune reaction in mice that might mask an eventual treatment effect.

Experimental

Male ApoE*3 Leiden mice were fed a cholesterol-rich high-fat diet to induce hypercholesterolemia. The diet contained 0.05% cholate (to improve intestinal cholesterol uptake and suppress bile acid synthesis, both leading to increased plasma cholesterol levels) and 1% cholesterol (as well as 20% casein, 1% choline chloride, 0.2% methionine, 15% cocoa butter, 40.5% sucrose, 10% cornstarch, 1% corn oil, 5.1% cellulose and 5.1% mineral mixture). They received the diet three weeks prior to surgery and the diet was continued throughout the entire experiment. The mice were given drinking water that was acidified to pH 2.8 with HCl. All animals received food and water ad libitum during the entire experiment.

Treatment

In this study experiments were performed with three different treatment groups. The groups were as follows:
  Control group, receiving vehicle only (phosphate buffered saline (PBS)) and undergoing vein graft surgery.
  Treatment group I, undergoing vein graft surgery and receiving recombinant human annexin A5 at a concentration 1 mg/kg/day via intraperitoneal injection, starting on the day of the surgery.
  Treatment group II, undergoing vein graft surgery and receiving recombinant murine annexin A5 at a concentration 1 mg/kg/day via intraperitoneal injection, starting on the day of the surgery.

Surgical Procedure of Vein Grafting

Mice were anesthetized before surgery by intraperitoneal administration of a combination of Midazolam, Medetomidine and Fentanyl. This cocktail of anaesthetics gives complete narcosis for at least one hour. After shaving the neck area and disinfecting the surgery area with alcohol (70%) a longitudinal 1 cm incision was made in the frontal side of the neck. The right common carotid artery was dissected free from its surroundings from the bifurcation at the distal end towards the proximal end. The vessel was ligated twice with an 8.0 silk ligature (B/BRAUN, Tuttlingen, Germany) and dissected between the middle ties. A cuff was placed over both ends after which these were everted over the cuffs and ligated with an 8.0 silk ligature. Littermates were used as donor for the inferior caval vein. The carefully harvested inferior caval vein was temporarily preserved in a 0.9% NaCl solution, containing 100 U/ml of heparin at 4° C., to prevent coagulation and was interpositioned between the ends of the artery. The connections were ligated together with an 8.0 silk suture. Pulsations confirmed successful engraftment. After surgery, anaesthesia was antagonized subcutaneously with Atipamezol (2.5 mg/kg, Roche, Woerden, The Netherlands) and Flumazenil (0.5 mg/kg Orion, Espoo, Finland). Animals were placed in a clean cage on top of a heating pad for at least 4 hours.

Sacrifice of the Animals

Sacrifice was performed as described in Example 3, except that the vein graft, rather than the cuffed artery, was harvested, fixed, sectioned and stained.

Blood Sampling

Blood sampling and cholesterol and total triglyceride analyses were performed as described in Example 3.

Analysis of Vein Graft Thickening

Vein graft thickening was quantified using 6 equally spaced perpendicular cut serial sections of the vein graft.

Leukocytes

The vascular composition was analyzed by immunocytochemistry and histomorphometric analysis. Leukocytes were identified by reactivity to anti-CD45 antibodies (Pharmingen, San Diego, USA) and were quantified as number of positive cells per high power field.

Results

Vein Graft Thickening

Figure 4:
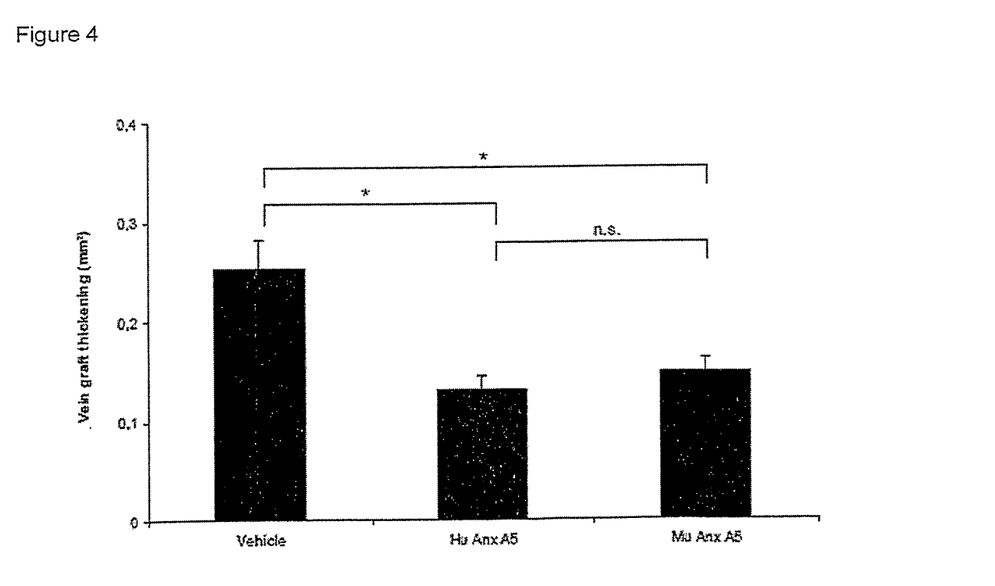
FIG. 4. Vein graft thickening of APOE*3-Leiden transgenic mice, fed a cholesterol-rich diet, 28 days after vein graft surgery and daily treatment with vehicle, recombinant human or murine annexin A5. Area between the lumen and adventitia is represented as mean±SEM (mm$^2$). n.s.: not significant.

To study the role of annexin A5 on vein graft thickening, recombinant human or murine annexin A5 (1 mg/kg, dissolved in 150 µl vehicle) was administered daily via intraperitoneal injection to the different groups (n=10 mice per group). A vehicle only group was used as control group (n=10 mice). Mean vein graft thickening, by measurement of the area between the lumen and adventitia, was quantified for each group 28 days after surgery. Vein graft thickening was significantly decreased by 48% to $0.13\pm0.01$ mm$^2$ (p=0.006) and by 40% to $0.15\pm0.01$ mm$^2$ (p=0.018) in recombinant human and murine annexin A5 treated groups, in comparison to the vehicle group ($0.25\pm0.05$ mm$^2$) (FIG. 4).

A larger luminal area was seen in the recombinant human ($0.44\pm0.03$ mm$^2$, p=0.126) and murine ($0.41\pm0.04$ mm$^2$, p=0.886) annexin A5 treated groups, in comparison to the vehicle group ($0.38\pm0.03$ mm$^2$).

Leukocytes

Figure 5:
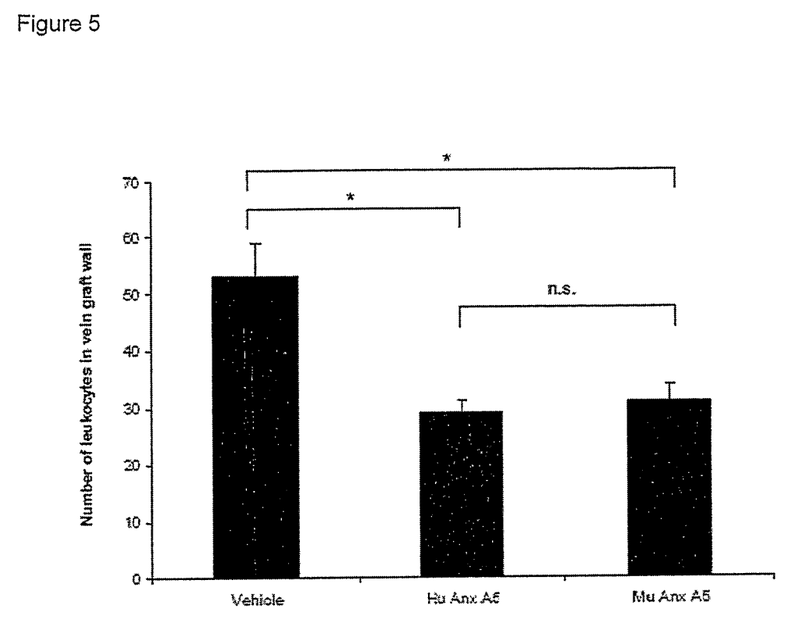
FIG. 5. Quantification of the number of leukocytes in the vein graft wall in APOE*3-Leiden transgenic mice, fed a cholesterol-rich diet, 28 days after vein graft surgery and daily treatment with vehicle, recombinant human or murine annexin A5. The number of cells is expressed as mean±SEM.

The number of leukocytes in the vein graft wall was counted after 28 days as a marker of inflammation and resulted in a significant decrease in the number of leukocytes of 45.8% in the recombinant human annexin A5 ($28.8\pm2.3$ cells, p=0.003) and of 41.8% in the recombinant murine annexin A5 ($30.9\pm3.0$ cells, p=0.025) treated groups in comparison to the vehicle group ($53.1\pm6.1$ cells) (FIG. 5).

Conclusion

The rapid development of a neointima in vein grafts is a clinical problem resulting in restenosis, i.e. the lumen of the grafted vein becomes reduced and blood flow restricted. This study clearly shows that annexin A5 treatment, using either human or murine annexin A5, effectively reduced the neointima growth in the vein grafts, and prevented lumen narrowing. The rapid development of a neointima is an inflammation driven process, and it is likely that the beneficial effects of annexin A5 were linked to the anti-inflammatory effects of the treatment (seen as a reduction in leukocyte accumulation in the grafts, and as shown in example 3). Both human and murine annexin A5 yielded similar results, showing that human annexin A5 did not trigger any non-specific immune reaction in the mice that could have masked the treatment effects. The results strongly support that annexin A5 is an effective treatment for the prevention of vein graft restenosis.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

PCT Appln. WO 02/067857
PCT Appln. WO 2005/099744
U.S. Pat. No. 6,602,282 (Assignee Avantec Vascular Corporation).
WO 99/17680 (Localmed Inc).
U.S. Pat. No. 5,922,020 (Localmed Inc).
US 2006/0083772 (DeWitt et al)
US2005/0037052 (Medtronic Vascular, Inc.)
Bhadra et al., (2002) *Pharmazie* 57, 5-29
Blindt et al (1999) *Int J Artif Organs* 22: 843-853
Bravata et al., *Ann. Intern. Med.*, 147(10):703-716, 2007.
Cederholm and Frostegard, *Ann. NY Acad. Sci.*, 1108:96-103, 2007.
Cederholm at al., *Arterioscler. Thromb. Vasc. Biol.*, 25(1): 198-203, 2005.
Harris et al., (2001) Clin Pharmacokinet 40, 539-551
Hirata et al (2006) *J. Amer. Soc. Echocardiography* 19:165-191
Nolte et al (2007) *Cardiovascular ultrasound* 5: 33
Jasti et al (2004) *Circulation* 110: 2831-2836
Kozlowski et al., (2001) *J Control Release* 72, 217-224
Kozlowski et al., (2001), *Biodrugs* 15, 419-429
Motwani and Topol, *Circulation,* 97:(9):916-931, 1998.
Ong and Serruys (2005) *Curr Issues Cardiol* 32: 372-377
Pires et al, *Vascul. Pharmacol.*, 44(5):257-264, 2006.
Rand, *J. Autoimmun.*, 15(2):107-111, 2000.
Reddy, (2001) Ann Pharmacother 34, 915-923
Roberts et al., (2002) Adv Drug Deliv Rev, 54, 459-476
Shen et al., *Am. J. Transplant.*, 7(11):2463-2471, 2007.
Smith Jr., et al., *J. Am. Coll. Cardiol.*, 47(1):216-235, 2006.
Teoh et al., *Gastroenterology,* 133(2):632-646, 2007.
Thiagarajan and Benedict, *Circulation,* 96(7):2339-2347, 1997.
Vermes, I., et al., *A novel assay for apoptosis. Flow cytometric detection of phosphatidylserine expression on early apoptotic cells using fluorescein labelled Annexin V.* J Immunol Methods, 1995. 184(1): p. 39-51
Veronese (2001) Biomaterials 22, 405-417
Vogt et al (2004) *European Heart Journal* 25: 1330-40.
Zhang et al., *Arterioscler. Thromb. Vasc. Biol.*, 24(12):2277-2283, 2004.
Zou et al., *Am. J. Pathol.*, 153(4):1301-1310, 1998.

What is claimed:

1. A method for the treatment of restenosis, wherein the restenosis is caused by neointima formation or neointimal thickening, in a patient that has been diagnosed with restenosis, wherein the method comprises:
administering a therapeutically effective amount of an active agent to the patient for a period of at least 2 weeks after diagnosis of restenosis, wherein the active agent is selected from the group consisting of an Annexin A5 polypeptide, a dimer of the Annexin A5 polypeptide, the Annexin A5 polypeptide that has been PEGylated, and a dimer of the Annexin A5 polypeptide that has been PEGylated;
wherein the Annexin A5 polypeptide consists of an amino acid sequence which has more than 95% sequence identity to the amino acid sequence of SEQ ID NO: 1 and which binds to phosphatidylserine on a biological membrane to a level that is at least 80% of that displayed by human Annexin A5 having the sequence of SEQ ID NO: 1 under the same conditions.

2. The method according to claim 1, wherein the restenosis is associated to a bypass graft.

3. The method according to claim 1, wherein the restenosis is associated to a catheter-based intervention.

4. The method of claim 1, wherein the restenosis is associated with the implantation of a stent.

5. The method of claim 1, wherein the therapeutically effective amount of the active agent is administered parenterally, intravenously, intra-arterially, intra-peritoneally, intra-muscularly, subcutaneously or is administered locally from a drug eluting stent.

6. The method of claim 1, wherein the active agent is administered in conjunction with a thrombolytic therapeutic.

7. The method of claim 1, wherein the Annexin A5 polypeptide is selected from the group consisting of:
a) human Annexin A5 consisting of the sequence of SEQ ID NO: 1;
b) a dimer of human Annexin A5 consisting of the sequence of SEQ ID NO: 1;
c) human Annexin A5 consisting of the sequence of SEQ ID NO: 1 that has been PEGylated; and
d) a dimer of human Annexin A5 consisting of the sequence of SEQ ID NO: 1 that has been PEGylated.

8. The method of claim 6 wherein the thrombolytic therapeutic is selected from the group consisting of aspirin, clopidogrel, triclopidine, tissue plasminogen activator, urokinase, and streptokinase.

9. The method of claim 1, wherein the administering is for a period of at least 1 month after diagnosis of restenosis.

10. The method of claim 9, wherein the administering is for a period of at least 2 months to at least 10 years after diagnosis of restenosis.

11. The method of claim 1, wherein the Annexin A5 polypeptide consists of an amino acid sequence which has more than 99% sequence identity to the amino acid sequence of SEQ ID NO: 1.

12. The method of claim 1, wherein the Annexin A5 polypeptide consists of the amino acid sequence of SEQ ID NO: 1.

13. The method of claim 1, wherein the method protects against worsening of the restenosis, or the restenosis worsens more gradually or to a reduced extent in the patient.

14. The method of claim 1, wherein the administering is for a period of at least 2 months after diagnosis of restenosis.

15. The method of claim 1, wherein the administering is for a period of at least 6 months after diagnosis of restenosis.

16. The method of claim 1, wherein the administering is for a period of at least 1 year after diagnosis of restenosis.

17. The method of claim 1, wherein the administering is for a period of at least 2 years after diagnosis of restenosis.

18. The method of claim 1, wherein the administering is for a period of at least 5 years after diagnosis of restenosis.

19. The method of claim 1, wherein the administering is for a period of at least 10 years after diagnosis of restenosis.

* * * * *